US012648906B2

(12) United States Patent
Ding et al.

(10) Patent No.: US 12,648,906 B2
(45) Date of Patent: Jun. 9, 2026

(54) FAT EMULSION DIALYSATE, AND PREPARATION METHOD AND USE THEREOF

(71) Applicant: SHANGHAI SUPERB MEDICAL TECHNOLOGY CO., LTD, Shanghai (CN)

(72) Inventors: Feng Ding, Shanghai (CN); Yifeng Wang, Shanghai (CN); Yuqi Shen, Shanghai (CN); Jiaolun Li, Shanghai (CN)

(73) Assignee: SHANGHAI SUPERB MEDICAL TECHNOLOGY CO., LTD, Shanghai (CN)

( * ) Notice: Subject to any disclaimer, the term of this patent is extended or adjusted under 35 U.S.C. 154(b) by 225 days.

(21) Appl. No.: 18/218,130

(22) Filed: Jul. 5, 2023

(65) Prior Publication Data

US 2023/0398071 A1     Dec. 14, 2023

Related U.S. Application Data

(63) Continuation of application No. PCT/CN2021/099563, filed on Jun. 11, 2021.

(30) Foreign Application Priority Data

Jan. 5, 2021     (CN) .......................... 202110008666.1
Apr. 21, 2023     (CN) .......................... 202310434321.1

(51) Int. Cl.
| | |
|---|---|
| *A61K 9/107* | (2006.01) |
| *A61K 47/10* | (2017.01) |
| *A61K 47/14* | (2017.01) |
| *A61K 47/24* | (2006.01) |
| *A61K 47/44* | (2017.01) |
| *A61P 7/08* | (2006.01) |

(52) U.S. Cl.
CPC .............. *A61K 9/107* (2013.01); *A61K 47/10* (2013.01); *A61K 47/14* (2013.01); *A61K 47/24* (2013.01); *A61K 47/44* (2013.01); *A61P 7/08* (2018.01)

(58) Field of Classification Search
CPC ........ A61K 9/107; A61K 47/10; A61K 47/14; A61K 47/24; A61K 47/44; A61P 7/08
See application file for complete search history.

(56) References Cited

FOREIGN PATENT DOCUMENTS

| | | | |
|---|---|---|---|
| CN | 1376460 A | | 10/2002 |
| CN | 1965806 A | * | 5/2007 |
| CN | 101190248 A | | 6/2008 |
| CN | 101244037 A | | 8/2008 |
| CN | 101312712 A | | 11/2008 |
| CN | 102348469 A | | 2/2012 |
| CN | 109589306 A | | 4/2019 |
| CN | 111821263 A | | 10/2020 |
| WO | WO 2020018512 A1 | | 1/2020 |

OTHER PUBLICATIONS

CN-1965806-A translated (Year: 2007).*
Timofte et al. (Dyselectrolytemia-mangement and implications in hemodialysis, Exp Ther Med, Nov. 2020, (Year: 2020).*
Shi et al. (Improved dialytic removal of protein-bound uremic toxins by intravenous lipid emulsion in chronic kidney disease rats, ndt , 2019 (Year: 2019).*
Shi Y.Y. et al, "Improved dialytic removal of protein-bound uremic toxins by intravenous lipid emulsion in chronic kidney disease rats", [Nephrol Dial Transplant], vol. 34, No. 11, May 9, 2019 (May 9, 2019), UK.
Shi, Xuefeng et al.,"Preliminary Examination on Removal of Protein-Bound Toxins by Hemolipodialysis", (Fudan University Journal of Medical Sciences),vol. 33, No. 2, Mar. 31, 2006 (Mar. 31, 2006), CN.

* cited by examiner

*Primary Examiner* — Robert A Wax
*Assistant Examiner* — John Seungjai Kwon
(74) *Attorney, Agent, or Firm* — IPRTOP LLC

(57) ABSTRACT

The present invention relates to the field of hemodialysis and peritoneal dialysis, in particular to a fat emulsion dialysate, and preparation method and the use thereof. Provided in the present invention is a fat emulsion dialysate, comprising a long-chain fat emulsion oil, a medium-chain triglyceride, an anti-oxidant, sodium oleate, glycerin, phospholipid, and a solvent. Compared with traditional dialysis, the fat emulsion dialysate provided by the present invention has a better advantage for protein-bound toxin removal. In addition, the fat emulsion dialysate not only has a simple preparation method and a low cost, but also has good stability and safety, and remains stable at room temperature for 14 days without obvious precipitation. Thus, the fat emulsion dialysate can become a hemodialysis dialysate or peritoneal dialysate with broad application prospects, and has good industrialization prospects.

20 Claims, 7 Drawing Sheets

FAT EMULSION DIALYSATE, AND PREPARATION METHOD AND USE THEREOF

CROSS REFERENCE TO RELATED APPLICATION

This is a continuation application claiming the benefit of priority to a pending PCT application PCT/CN2021/099563, field on Jun. 11, 2021, entitled "FAT EMULSION DIALYSATE, AND PREPARATION METHOD AND USE THEREOF", which claims to the priority of a Chinese Patent Application No. CN 202110008666.1, field on Jan. 5, 2021, and Chinese Patent Application No. CN 202310434321.1, field on Apr. 21, 2023, entitled "USE OF FAT EMULSION IN PREPARATION OF PERITONEAL DIALYSATE FOR REMOVAL OF PROTEIN-BOUND TOXINS", the disclosure of all are incorporated herein by reference in their entireties, including any appendices or attachments thereof, for all purpose.

FIELD OF TECHNOLOGY

The present invention relates to the field of hemodialysis and peritoneal dialysis, particularly, to a fat emulsion dialysate and a preparation method and use thereof.

BACKGROUND

Protein-bound toxins refer to toxins that exist mostly in a non-dissociated form in plasma, and accumulate due to abnormal metabolism in a pathological state. Few protein-bound toxins are free in the blood, and protein-bound toxins cannot pass through the dialysis membrane, therefore, it is difficult to remove them by traditional hemodialysis technology. Accumulation of protein-bound uremic toxins (PBUTs) in patients with end-stage renal disease is associated with an increase in the incidence of uremic complications, where it has been proved that indoxyl sulfate and p-cresol sulfate are closely associated with an increase in all-cause mortality and cardiovascular disease incidence in patients with chronic kidney disease (CKD). Removal of uremic PBUTs is a difficult problem in blood purification technology. PBUTs are usually small molecular organic anions, in which organic anions with an aromatic phenyl ring mainly bind closely to site II of serum albumin in blood circulation, such as p-cresol sulfate (PCS), indoxyl sulfate (IS) and indolyl-3-acetic acid (3-IAA). For patients with abnormal liver function, bilirubin level is an independent risk factor affecting the death of patients with acute-on-chronic liver failure. The accumulated protein-bound toxins play an important role in the secondary development of serious complications such as renal failure, hepatic encephalopathy, and circulatory disorder. Artificial liver support technology (ALSS), represented by albumin dialysis (AD), came into being. ALSS can remove protein-bound toxic substances and metabolites such as bilirubin and bile acids accumulated in patients with liver failure to improve the internal environment, thus helping the patients to get through the acute phase until liver transplantation or self-liver function recovery.

During the treatment of albumin dialysis, free protein-bound toxins in blood diffuse into the dialysate so that the concentration of free toxins at the blood side decreases and the association/dissociation balance of toxin-albumin moves to the dissociation direction, thereby dissociating and releasing the toxins and achieving a new balance. The amount of toxins binding to albumin in the dialysate determines the amount of toxins to be removed. Albumin dialysis combines the advantage of protein-bound toxin removal by plasma infusion with good biocompatibility of hemodialysis, and is in nature a removal based on diffusion and adsorption. Even though albumin dialysis can effectively clear water-soluble toxins and protein-bound toxins and correct the internal environmental disorder in patients to mitigate the clinical symptoms, its clinical application is restricted by the resource of human albumin and the treatment cost. By looking for a blood purification technology which can substitute for albumin dialysis, has a low cost, and can effectively clear the protein-bound toxins, it will help to increase the removal of PBUTs in patients with uremia, and help to alleviate symptoms of patients with liver functional failure.

SUMMARY

In view of the shortcomings of the prior technology as set forth above, an object of the present invention is to provide a fat emulsion dialysate and a preparation method and use thereof for addressing the problems existing in the prior technology.

To achieve the above object and other objects, in an aspect, the present invention provides a fat emulsion dialysate, comprising a long-chain fat emulsion oil, a medium-chain triglyceride, an anti-oxidant, sodium oleate, glycerin, phospholipid, and a solvent.

In some embodiments of the present invention, the fat emulsion dialysate comprises, by weight percent, 3 to 15% of the long-chain fat emulsion oil;

1.5 to 9% of the medium-chain triglyceride;

0.05 to 0.3% of the anti-oxidant;

0.05 to 0.3% of sodium oleate;

0.2 to 2% of glycerin;

1 to 12% of phospholipid; and 65 to 95% of the solvent.

In some embodiments of the present invention, the long-chain fat emulsion oil is selected from one or more of olive oil and soybean oil; and/or a total content of acid and decanoic acid in the medium-chain triglyceride is ≥99 wt %, preferably ≥99.5 wt %, and more preferably ≥99.9 wt %; and/or the anti-oxidant is one or a combination of α-tocopherol and squalene.

In some embodiments of the present invention, the phospholipid is selected from lecithins, preferably one or a combination of soybean lecithin and egg yolk lecithin.

In some embodiments of the present invention, the solvent is an aqueous solvent. The aqueous solvent comprises water, and further comprises one or more of sodium chloride, potassium chloride, calcium chloride, magnesium chloride, and glucose.

In some embodiments of the present invention, the fat emulsion dialysate is an oil-in-water system.

In some embodiments of the present invention, a fat emulsion particle size in the fat emulsion dialysate is from 150 to 500 nm.

In another aspect, the present invention provides a method for preparing the fat emulsion dialysate, comprising: providing an oil phase and an aqueous phase, mixing the oil phase with the aqueous phase, and homogenizing to provide the fat emulsion dialysate.

In some embodiments of the present invention, the mixing and/or homogenizing is carried out at a temperature of 50 to 90° C.; and/or the oil phase and the aqueous phase are thoroughly mixed by a high-speed shearing at a high-speed shear rate of 10000 to 20000 rpm and a shear time of 5 to 30 min; and/or the homogenizing is carried at a pressure of 200 to 1000 bar.

In another aspect, the present invention provides a use of the fat emulsion dialysate for preparation of a hemodialysis dialysate.

In another aspect, the present invention provides a fat emulsion combination reagent comprising a first reagent and a second reagent, where the first reagent comprises a long-chain fat emulsion oil, a medium-chain triglyceride, an anti-oxidant, sodium oleate, phospholipid, and a first solvent, the second reagent comprises an electrolyte, a penetrating agent, a base donor, and a second solvent, the first reagent is separated from the second reagent, and the first reagent and the second reagent are mixed prior to use.

In some embodiments of the present invention, the first reagent is put in a first chamber bag and the second reagent is put in at least one second chamber bag.

In some embodiments of the present invention, the number of the second chamber bag is 1 or 2.

In further embodiments of the present invention, when the base donor of the second reagent is sodium lactate, the second reagent is put in one second chamber bag; when the base donor of the second reagent is sodium bicarbonate or a mixture of sodium lactate and sodium bicarbonate, the penetrating agent and a first portion of the electrolyte of the second reagent are put in one second chamber bag, and the base donor and a second portion of the electrolyte of the second reagent are put in another second chamber bag.

In some embodiment of the present invention, the first portion of the electrolyte comprises calcium chloride and magnesium chloride, and the second portion of the electrolyte is sodium chloride.

In some embodiments of the present invention, the fat emulsion combination reagent comprises 3 to 15 parts by weight of the long-chain fat emulsion oil;
1.5 to 9 parts by weight of the medium-chain triglyceride;
0.05 to 0.3 parts by weight of the anti-oxidant;
0.05 to 0.3 parts by weight of sodium oleate;
1 to 12 parts by weight of phospholipid;
80 to 95 parts by weight of the first solvent, where the first solvent is an aqueous solvent;
0.2 to 0.8 parts by weight of the electrolyte;
0.1 to 10 parts by weight of the penetrating agent;
0.2 to 0.6 parts by weight of the base donor; and
5 to 20 parts by weight of the second solvent, where the second solvent is an aqueous solvent.

In some embodiments of the present invention, the long-chain fat emulsion oil is selected from one or more of palm oil, flaxseed oil, olive oil, and soybean oil.

In some embodiments of the present invention, the medium-chain triglyceride is selected from one or a combination of caprylic acid and decanoic acid.

In further embodiments of the present invention, when the medium-chain triglyceride comprises caprylic acid and decanoic acid, a total content of caprylic acid and decanoic acid is no less than 99 wt %, preferably no less than 99.5 wt %, more preferably no less than 99.9 wt %.

In some embodiments of the present invention, the anti-oxidant is selected from one or more of ascorbyl palmitate, α-tocopherol, β-tocopherol, squalene, and carotene.

In some embodiments of the present invention, the phospholipid is selected from lecithins, preferably, one or a combination of soybean lecithin and egg yolk lecithin.

In some embodiments of the present invention, the first solvent is water.

In some embodiments of the present invention, the second solvent is water.

In some embodiments of the present invention, the penetrating agent is selected from one or more of glucose, mannitol, polysaccharides, and amino acids.

In some embodiments of the present invention, the electrolyte comprises sodium chloride, magnesium chloride, and calcium chloride.

In further embodiments of the present invention, the electrolyte comprises 0.2 to 0.8 parts by weight of sodium chloride;
0.002 to 0.008 parts by weight of magnesium chloride; and
0.01 to 0.03 parts by weight of calcium chloride.

In some embodiments of the present invention, the base donor is selected from one or a combination of sodium lactate and sodium bicarbonate.

In some embodiments of the present invention, the fat emulsion combination reagent is an oil-in-water system.

In some embodiments of the present invention, a fat emulsion particle size in the fat emulsion combination reagent is 150 to 500 nm.

In another aspect, the present invention provides a method for preparing the fat emulsion combination reagent as described above, the method comprises providing the long-chain fat emulsion oil, the medium-chain triglyceride, the anti-oxidant, sodium oleate, and phospholipid, mixing the long-chain fat emulsion oil, the medium-chain triglyceride, the anti-oxidant, sodium oleate, and phospholipid with the first solvent, shearing and homogenizing to form the first reagent; dissolving the electrolyte, the penetrating agent, and the base donor in the second solvent to form the second reagent, and separating the first reagent from the second reagent to provide the fat emulsion combination reagent.

In some embodiments of the present invention, the mixing and/or homogenizing is carried out at a temperature of 50 to 90° C.;

and/or, the first reagent is thoroughly mixed by the shearing at a shear rate of 10000 to 20000 rpm and a shear time of 5 to 30 min;
and/or, the homogenizing is carried at a pressure of 200 to 1500 bar.

In another aspect, the present invention provides a use of a fat emulsion in preparation of peritoneal dialysate.

In some embodiments of the present invention, the fat emulsion is the fat emulsion combination reagent.

In some embodiments of the present invention, the use comprises mixing a first reagent with the second reagent to provide a peritoneal dialysate.

In further embodiments of the present invention, after the mixing of the first reagent and the second reagent, a pH of the mixed solution ranges from 5.0 to 8.0;

and/or, an osmotic pressure of the mixed solution ranges from 300 to 500 mOsmol/L.

In further embodiments of the present invention, the use comprises putting the first reagent of the fat emulsion combination reagent described above in a first chamber bag, and putting the second reagent in at least one second chamber bag. When the base donor of the second reagent is sodium lactate, the second reagent is put in a second chamber bag; when the base donor of the second reagent is sodium bicarbonate or a mixture of sodium lactate and sodium bicarbonate, the penetrating agent and the first portion of the electrolyte of the second reagent are put in a second chamber bag, and the base donor and the second portion of the electrolyte of the second reagent are put in another second chamber bag.

As described above, the use of fat emulsion in preparation of peritoneal dialysate for the removal of protein-bound toxins provided by the present invention has the following beneficial effects:

(1) The fat emulsion provided by the present invention is a combination reagent that has an adsorption effect on protein-bound toxins and good biocompatibility, thereby improving the clearance of protein-bound toxins by peritoneal dialysis.

(2) When the fat emulsion provided by the present invention serves as a peritoneal dialysate, free protein-bound toxins in the peritoneal dialysate are continuously adsorbed, and more free protein-bound toxins from the blood side tend to enter the peritoneal dialysate side and be encapsulated by the fat emulsion, thereby improving the removal of protein-bound toxins by peritoneal dialysis.

(3) When the fat emulsion provided by the present invention serves as a peritoneal dialysate, the therapeutic effect of peritoneal dialysis is improved, cardiovascular complications in uremic patients are reduced, and potential value for improving the living quality of uremic patients is bolstered.

DETAILED DESCRIPTION

Figure 1:
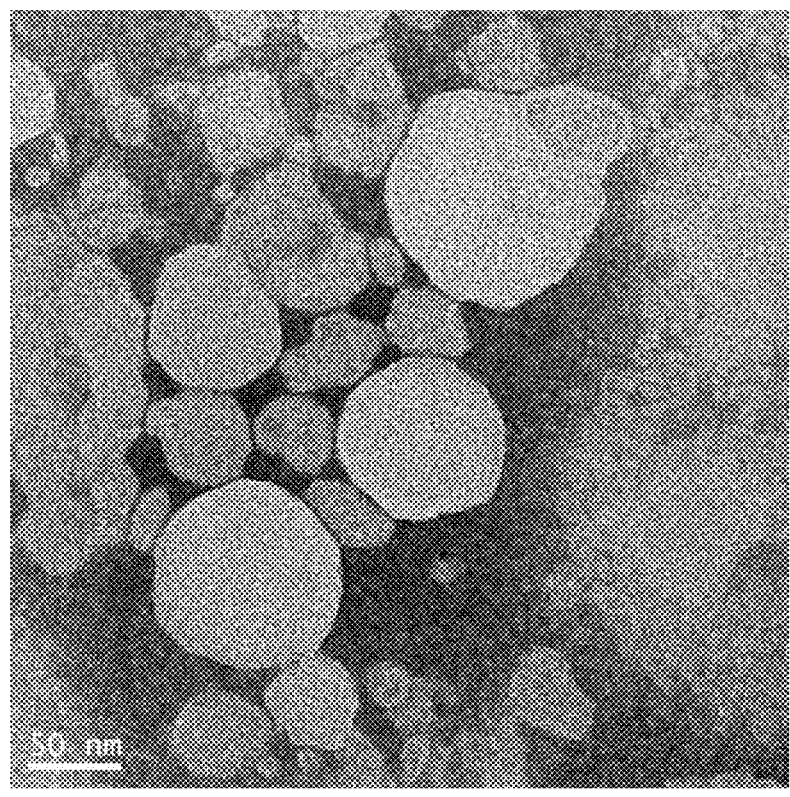
FIG. 1 shows a schematic diagram of fat emulsion particles observed by a transmission electron microscope in Example 2 of the present invention.

In order to make the purpose, technical solution, and beneficial technical effect of the present invention clearer, the present invention will be further described in detail by reference to the examples hereinafter. Persons skilled in the art can easily understand other advantages and efficacy of the present invention from the disclosure of the description.

Through a great number of practical research, the inventor provides a fat emulsion dialysate which can serve as a hemodialysis dialysate or a peritoneal dialysate, and have a stronger binding and removal capacity to protein-bound toxins.

In a first aspect, the present invention provides a fat emulsion dialysate, comprising a long-chain fat emulsion oil, a medium-chain triglyceride, an anti-oxidant, sodium oleate, glycerin, phospholipid, and a solvent. The fat emulsion dialysate is commonly an emulsion system which utilizes a small-particle-sized oil phase as adsorptive material in dialysate to effectively enhance the binding capacity of the dialysate system to the protein-bound toxins (e.g., p-cresol sulfate (PCS), indoxyl sulfate (IS), indolyl-3-acetic acid (3-IAA), and the like), thereby effectively improving the protein-bound toxin removal capacity of the dialysate.

The fat emulsion dialysate provided by the first aspect of the present invention may comprise 3 to 15%, 3 to 4%, 4 to 5%, 5 to 6%, 6 to 7%, 7 to 8%, 7 to 9%, 9 to 10%, 10 to 11%, 11 to 12%, 12 to 13%, 13 to 14%, or 14 to 15% of the long-chain fat emulsion oil. The long-chain fat emulsion oil generally refers to a class of compounds comprising 17, 18, or 19 carbon atoms in the carbon chain of its primary ingredient fatty acid. In the fat emulsion dialysate, the long-chain fat emulsion oil mainly serves as one of the oil phase components. An appropriate amount of the long-chain fat emulsion oil can reduce the content of the oil phase to reduce the cost under the premise of ensuring the toxin removal effect. The long-chain fat emulsion oil is commonly pharmaceutical grade so that it can be suitable for the preparation of a dialysate. For example, it can meet the standards of the Chinese Pharmacopoeia 2015 edition, Second Volume. In particular, suitable long-chain fat emulsion oils may be one or more of olive oil, soybean oil, and the like.

The fat emulsion dialysate provided by the first aspect of the present invention may comprise, by weight percent, 1.5 to 9%, 1.5 to 2%, 2 to 2.5%, 2.5 to 3%, 3 to 3.5%, 3.5 to 4%, 4 to 4.5%, 4.5 to 5%, 5 to 5.5%, 5.5 to 6%, 6 to 6.5%, 6.5 to 7%, 7 to 7.5%, 7.5 to 8%, 8 to 8.5%, or 8.5 to 9% of the medium-chain triglyceride. The medium-chain triglyceride generally refers to a class of compounds with C8 to C10 fatty acids as primary ingredients (e.g., octanoic acid, decanoic acid, etc.), which can be extracted from coconut oil and/or palm oil. In the fat emulsion dialysate, the medium-chain triglyceride mainly serves as one of the oil phase components. In the fat emulsion dialysate, the presence of the medium-chain triglyceride generally helps to improve the oxidation stability of the oil phase. The medium-chain triglyceride is commonly pharmaceutical grade so that it can be suitable for the preparation of the dialysate. For example, it can meet the drug quality standards (YBH03422008). As another example, in the medium-chain triglyceride, the content of octanoic acid may be 55.4 to 61.4 wt %, 55.4 to 56.4 wt %, 56.4 to 57.4 wt %, 57.4 to 58.4 wt %, 58.4 to 59.4 wt %, 59.4 to 60.4 wt %, or 60.4 to 61.4 wt %; the content of decanoic acid may be 38.5 to 44.5 wt %, 38.5 to 39.5 wt %, 39.5 to 40.5 wt %, 40.5 to 41.5 wt %, 41.5 to 42.5 wt %, 42.5 to 43.5 wt %, or 43.5 to 44.5 wt %; and a total content of octanoic acid and decanoic acid is generally ≥99 wt %, ≥99.5 wt %, or ≥99.9 wt %.

The fat emulsion dialysate provided by the first aspect of the present invention may comprise, by weight percent, 0.05 to 0.3%, 0.05 to 0.1%, 0.1 to 0.15%, 0.15 to 0.2%, 0.2 to 0.25%, or 0.25 to 0.3% of the anti-oxidant. In the fat emulsion dialysate, the anti-oxidant mainly serves as one of the oil phase components. The anti-oxidant can effectively improve the colloidal stability of the fat emulsion. The anti-oxidant can be various anti-oxidants suitable for the preparation of the dialysate in the art. For example, the anti-oxidant may be one or more of α-tocopherol, β-tocopherol, and squalene (triacontahexaene).

The fat emulsion dialysate provided by the first aspect of the present invention may comprise, by weight percent, 0.05 to 0.3%, 0.05 to 0.1%, 0.1 to 0.15%, 0.15 to 0.2%, 0.2 to 0.25%, or 0.25 to 0.3% of sodium oleate. In the fat emulsion dialysate, the sodium oleate mainly serves as one of the aqueous phase components. The presence of sodium oleate serving as a supplement to the emulsifying capacity of phospholipid can improve the dispersibility and colloidal stability of the fat emulsion particles.

The fat emulsion dialysate provided by the first aspect of the present invention may comprise, by weight percent, 0.2 to 2%, 0.2 to 0.4%, 0.4 to 0.6%, 0.6 to 0.8%, 0.8 to 1%, 1 to 1.2%, 1.2 to 1.4%, 1.4 to 1.6%, 1.6 to 1.8%, or 1.8 to 2% of glycerin. In the fat emulsion dialysate, glycerin mainly serves as one of the aqueous phase components. The presence of glycerin can regulate the osmotic pressure of the fat emulsion dialysate.

The fat emulsion dialysate provided by the first aspect of the present invention may comprise, by weight percent, 1 to 12%, 1 to 2%, 2 to 3%, 3 to 4%, 4 to 5%, 5 to 6%, 6 to 7%, 7 to 8%, 8 to 9%, 9 to 10%, 10 to 11%, or 11 to 12% of phospholipid. In the fat emulsion dialysate, the phospholipid mainly serves as one of the aqueous phase components. In the fat emulsion dialysate, the increase of phospholipid content can generally result in an increase in the direct adsorption rate between the dialysate and the protein-bound toxins. The phospholipid may be various phospholipids suitable for the preparation of the dialysate, e.g., those meeting the standards of the U.S. Pharmacopoeia, the Japanese Pharmacopoeia, the European Pharmacopoeia, the Chinese Pharmacopoeia, and the like. In particular, suitable phospholipids may be lecithins (such as soybean lecithin and egg yolk lecithin) or the like.

The fat emulsion dialysate provided by the first aspect of the present invention may comprise, by weight percent, 65 to 95% of solvent, 65 to 70% of solvent, 70 to 75% of solvent, 75 to 80% of solvent, 80 to 85% of solvent, 85 to 90% of solvent, or 90 to 95% of solvent. In the fat emulsion dialysate, the aqueous components can generally dissolve in the solvent and constitute the aqueous phase of the emulsion system. In the fat emulsion dialysate, the solvent is generally an aqueous solvent. The aqueous solvent commonly comprises water, and water is commonly the main component of the aqueous solvent. In addition to water, the aqueous solvent can further comprise some components which can be introduced into the dialysate to meet the safety requirement of dialysis treatment. For example, the aqueous can further comprise one or more of sodium chloride (0.2 wt % to 0.8 wt %), potassium chloride (≤0.01 wt %), calcium chloride (0.01 wt % to 0.05 wt %), magnesium chloride (0.005 wt % to 0.03 wt %), glucose (0.15 wt % to 0.25 wt %) and the like.

In the fat emulsion dialysate provided by the first aspect of the present invention, the fat emulsion dialysate is commonly an oil-in-water system (O/W system), i.e., an emulsion system in which oil serving as an internal phase is dispersed in water serving as a continuous external phase. The oil phase is commonly uniformly distributed in the fat emulsion dialysate. The particle size of the oil phase (fat emulsion) may be appropriately 150 to 500 nm, 150 to 200 nm, 200 to 250 nm, 250 to 300 nm, 300 to 350 nm, 350 to 400 nm, 400 to 450 nm, or 450 to 500 nm.

In a second aspect, the present invention provides a method for preparing the fat emulsion dialysate provided by the first aspect of the present invention. On the basis that a formula of the fat emulsion dialysate is known, persons skilled in the art can properly select a method for preparing the fat emulsion dialysate. For example, the method may comprise providing an oil phase and an aqueous phase, mixing the oil phase with the aqueous phase, and homogenizing the mixture to provide the fat emulsion dialysate. As another example, when mixing and/or homogenizing, the temperature of the system may be 50 to 90° C., 50 to 60° C., 60 to 70° C., 70 to 80° C., or 80 to 90° C. As another example, the oil phase and the aqueous phase may be thoroughly mixed by high-speed shearing. The shear rate may be 10000 to 20000 rp/min, 10000 to 15000 rp/min, or 15000 to 20000 rp/min, and the shear time may be 5 to 30 min, 10 to 20 min, 5 to 10 min, 10 to 12 min, 12 to 14 min, 14 to 16 min, 16 to 18 min, 18 to 20 min, 20 to 25 min, or 25 to 30 min. As another example, the pressure condition of the homogenizing is 200 to 1000 bar, 200 to 400 bar, 400 to 600 bar, 600 to 800 bar, or 800 to 1000 bar. As another example, the pressure of the homogenizing may gradiently increase, and the homogenizing may be performed many times (e.g., 2 to 4 times) at the same pressure.

In a third aspect, the present invention provides a use of the fat emulsion dialysate provided by the first aspect of the present invention for preparation of a hemodialysis dialysate. As described above, the small-particle-sized oil phase of the system is utilized as adsorption material in the dialysate to effectively enhance the binding capacity of the dialysate system to the protein-bound toxins, so that the protein-bound toxin removal of the dialysate is improved, and the dialysate can be used for preparing the hemodialysis dialysate.

In a fourth aspect, the present invention provides a fat emulsion combination reagent comprising a first reagent and a second reagent, where the first reagent comprises a long-chain fat emulsion oil, a medium-chain triglyceride, an anti-oxidant, sodium oleate, phospholipid, and a first solvent, the second reagent comprises an electrolyte, a penetrating agent, a base donor, and a second solvent, the first reagent is separated from the second reagent, and the first reagent and the second reagent are mixed prior to use.

For the fat emulsion combination reagent provided by the fourth aspect of the present invention, the first reagent is put in a first chamber bag, and the second reagent is put in at least one second chamber bag.

The first chamber bag and the second chamber bag are conventional medical infusion chamber bags used in clinical. Adjacent chambers are separated from each other by non-permanent seals, to facilitate mixing prior to use.

In one embodiment, the first chamber bag has a single chamber, the second chamber bag may have one or more chambers, for example, double chambers or multi-chambers, and the number of the second chamber bag is preferably 1 or 2.

In a preferred embodiment, when the base donor of the second reagent is sodium lactate, the second reagent is put in one second chamber bag; when the base donor of the second reagent is sodium bicarbonate or a mixture of sodium lactate and sodium bicarbonate, the penetrating agent and a first portion of the electrolyte of the second reagent are put in one second chamber bag, and the base donor and a second portion of the electrolyte of the second reagent are put in another second chamber bag.

Specifically, the first portion of the electrolyte comprises calcium chloride and magnesium chloride; and the second portion of the electrolyte is sodium chloride.

The fat emulsion combination reagent provided by the fourth aspect of the present invention is commonly an emulsion system that utilizes a small-particle-sized oil phase as adsorptive material in peritoneal dialysis to effectively enhance the binding capacity of the peritoneal dialysate system to the protein-bound toxins (e.g., p-cresol sulfate (PCS), indoxyl sulfate (IS), and the like), thereby effectively improving the protein-bound toxin removal capacity of the peritoneal dialysate.

The fat emulsion combination reagent provided by the fourth aspect of the present invention may comprise 3 to 15, 3 to 4, 4 to 5, 5 to 6, 6 to 7, 7 to 8, 7.5 to 8.5, 7.9 to 8.1, 7.5 to 8.08, 8.08 to 8.5, 7 to 9, 9 to 10, 10 to 11, 11 to 12, 12 to 13, 13 to 14, or 14 to 15 parts by weight of the long-chain fat emulsion oil. The long-chain fat emulsion oil generally refers to a class of compounds containing 17, 18, or 19 carbon atoms in the carbon chain of its primary ingredient fatty acid. An appropriate amount of the long-chain fat emulsion oil can reduce the content of the oil phase to reduce the cost under the premise of ensuring the toxin removal effect. The long-chain fat emulsion oil is commonly pharmaceutical grade so that it is suitable for the preparation of a dialysate. For example, it can meet the standards of the Chinese Pharmacopoeia 2015 edition, Second Volume. Suitable long-chain fat emulsion oil is selected from one or more of palm oil, flaxseed oil, olive oil, and soybean oil.

The fat emulsion combination reagent provided by the fourth aspect of the present invention may comprise 1.5 to 9, 1.5 to 2, 2 to 2.5, 2.5 to 3, 3 to 3.5, 3.5 to 4, 3.8 to 4.04, 4.04 to 4.3, 3.9 to 4.1, 4 to 4.5, 4.5 to 5, 5 to 5.5, 5.5 to 6, 6 to 6.5, 6.5 to 7, 7 to 7.5, 7.5 to 8, 8 to 8.5, or 8.5 to 9 parts by weight of the medium-chain triglyceride. The medium-chain triglyceride generally refers to a class of compounds with C8 to C10 fatty acids as primary ingredients (e.g., octanoic acid, decanoic acid, etc.), which can be extracted from coconut oil and/or palm oil. In the fat emulsion combination reagent, the presence of the medium-chain triglyceride generally helps to improve the oxidation stability. The medium-chain triglyceride is commonly pharmaceutical grade so that it is suitable for the preparation of peritoneal dialysate. For example, it can meet the drug quality standards (YBH03422008). In some embodiments of the present invention, the medium-chain triglyceride is selected from one or a combination of caprylic acid and decanoic acid.

In one embodiment, when the medium-chain triglyceride comprises caprylic acid and decanoic acid, a total content of caprylic acid and decanoic acid is no less than 99 wt %, preferably no less than 99.5 wt %, more preferably no less than 99.9 wt %.

The fat emulsion combination reagent provided by the fourth aspect of the present invention may comprise 0.05 to 0.3, 0.05 to 0.1, 0.08 to 0.097, 0.097 to 0.12, 0.09 to 0.11, 0.1 to 0.15, 0.15 to 0.2, 0.2 to 0.25, or 0.25 to 0.3 parts by weight of the anti-oxidant. In the fat emulsion combination reagent, the anti-oxidant can effectively improve the colloidal stability of the fat emulsion. The anti-oxidant can be various anti-oxidants suitable for the preparation of the peritoneal dialysate in the art. For example, the anti-oxidant may be one or more of $\alpha$-tocopherol, $\beta$-tocopherol, squalene (triacontahexaene), carotene, etc.

The fat emulsion combination reagent provided by the fourth aspect of the present invention may comprise 0.05 to 0.3, 0.05 to 0.1, 0.07 to 0.086, 0.086 to 0.1, 0.08 to 0.09, 0.1 to 0.15, 0.15 to 0.2, 0.2 to 0.25, or 0.25 to 0.3 parts by weight of sodium oleate. In the fat emulsion combination reagent, the presence of sodium oleate serving as a supplement to the emulsifying capacity of phospholipid can improve the dispersibility and colloidal stability of the fat emulsion particles.

The fat emulsion combination reagent provided by the fourth aspect of the present invention may comprise 1 to 12, 1 to 2, 2 to 3, 3.5 to 3.67, 3.67 to 3.8, 3.6 to 3.7, 3 to 4, 4 to 5, 5 to 6, 6 to 7, 7 to 8, 8 to 9, 9 to 10, 10 to 11, or 11 to 12 parts by weight of phospholipid. In fat emulsion combination reagents, the increase of phospholipid content can generally result in an increase in the direct adsorption rate between the peritoneal dialysate and the protein-bound toxins. The phospholipid may be various phospholipids suitable for the preparation of the peritoneal dialysate, e.g., those meeting the standards of the U.S. Pharmacopoeia, the Japanese Pharmacopoeia, the European Pharmacopoeia, the Chinese Pharmacopoeia, and the like. In particular, suitable phospholipids may be lecithins (such as soybean lecithin and egg yolk lecithin) or the like.

The fat emulsion combination reagent provided by the fourth aspect of the present invention may comprise 80 to 95, 80 to 85, 85 to 90, 90 to 95, 80 to 90, or 85 to 95 parts by weight of the first solvent. The first solvent is usually an aqueous solvent, with water acting as the main component of the aqueous solvent. The water is deionized water.

The fat emulsion combination reagent provided by the fourth aspect of the present invention may also comprise the electrolyte, where the electrolyte comprises sodium chloride, magnesium chloride, and calcium chloride. The fat emulsion combination reagent provided by the present invention may comprise 0.2 to 0.8 parts by weight of the electrolyte. Specifically, the electrolyte may comprise 0.2 to 0.8, 0.2 to 0.4, 0.4 to 0.5, 0.5 to 0.6, 0.6 to 0.7, or 0.7 to 0.8 parts by weight of sodium chloride, 0.01 to 0.03, 0.01 to 0.014, 0.014 to 0.016, 0.016 to 0.018, 0.018 to 0.020, 0.020 to 0.024, or 0.024 to 0.030 parts by weight of calcium chloride, and 0.002 to 0.008, 0.002 to 0.004, 0.004 to 0.005, 0.005 to 0.006, 0.006 to 0.007, or 0.007 to 0.008 parts by weight of magnesium chloride.

The fat emulsion combination reagent provided by the fourth aspect of the present invention may comprise 0.1 to 10, 0.1 to 1.0, 1.0 to 2.0, 2.0 to 3.0, 3.0 to 4.0, 4.0 to 5.0, 5.0 to 6.0, 6.0 to 7.0, 7.0 to 8.0, 8.0 to 9.0, or 9.0 to 10.0 parts by weight of the penetrating agent. The penetrating agent is selected from one or more of glucose, mannitol, polysaccharides, and amino acids.

The fat emulsion combination reagent provided by the fourth aspect of the present invention may also comprise a base donor, where the base donor is selected from one or a combination of sodium lactate and sodium bicarbonate. The fat emulsion combination reagent provided by the present invention may comprise 0.2 to 0.6 parts by weight of the base donor. Specifically, the base donor may comprise 0.2 to 0.6, 0.2 to 0.25, 0.25 to 0.30, 0.30 to 0.35, 0.35 to 0.38, 0.38 to 0.41, 0.41 to 0.44, 0.44 to 0.47, 0.47 to 0.50, or 0.50 to 0.60 parts by weight of sodium lactate, and/or 0.2 to 0.6, 0.2 to 0.25, 0.25 to 0.30, 0.30 to 0.35, 0.35 to 0.38, 0.38 to 0.41, 0.41 to 0.44, 0.44 to 0.47, 0.47 to 0.50, or 0.50 to 0.60 parts by weight of sodium bicarbonate.

The fat emulsion combination reagent provided by the fourth aspect of the present invention may comprise 5 to 20, 5 to 10, 10 to 15, 15 to 20, 5 to 15, or 10 to 20 parts by weight of the second solvent. The second solvent is usually an aqueous solvent, with water acting as the main component of the aqueous solvent. The water is deionized water.

The second reagent described above is a concentrated liquid of peritoneal dialysate, to which the first reagent, i.e. the fat emulsion solution, is added and mixed to form a clinical peritoneal dialysate. The protein-bound toxin removal ability is further improved on the basis of maintaining the therapeutic effect of traditional peritoneal dialysate.

The fat emulsion combination reagent provided by the fourth aspect of the present invention is commonly an oil-in-water system (O/W system), i.e., an emulsion system in which oil serving as an internal phase is dispersed in water serving as a continuous external phase. The oil phase is commonly uniformly distributed in the fat emulsion combination reagent. The particle size of the oil phase may be appropriately 150 to 500 nm, 150 to 200 nm, 200 to 250 nm, 250 to 300 nm, 300 to 350 nm, 350 to 400 nm, 400 to 450 nm, or 450 to 500 nm.

In a fifth aspect, the present invention provides a method for preparing the fat emulsion combination reagent provided by the fourth aspect of the present invention. On the basis that a formula of the fat emulsion combination reagent is known, persons skilled in the art can properly select a method for preparing the fat emulsion combination reagent. For example, the method may comprise providing the long-chain fat emulsion oil, the medium-chain triglyceride, the anti-oxidant, sodium oleate, and phospholipid, mixing the long-chain fat emulsion oil, the medium-chain triglyceride, the anti-oxidant, sodium oleate, and phospholipid with the first solvent, shearing and homogenizing to form the first reagent; dissolving the electrolyte, the penetrating agent, and the base donor in the second solvent to form the second reagent, and separating the first reagent from the second reagent to provide the fat emulsion combination reagent. As another example, when mixing and/or homogenizing, the temperature of the system may be 50 to 90° C., 50 to 60° C., 60 to 70° C., 70 to 80° C., or 80 to 90° C. As another example, the first reagent may be thoroughly mixed by high-speed shearing. The shear rate may be 10000 to 20000 rp/min, 10000 to 15000 rp/min, or 15000 to 20000 rp/min, and the shear time may be 5 to 30 min, 10 to 20 min, 5 to 10 min, 10 to 12 min, 12 to 14 min, 14 to 16 min, 16 to 18 min, 18 to 20 min, 20 to 25 min, or 25 to 30 min. As another example, the pressure condition of the homogenizing is 200 to 1500 bar, 200 to 400 bar, 400 to 600 bar, 600 to 800 bar, 800 to 1200 bar, or 1200 to 1500 bar. As another example, the pressure of the homogenizing may gradiently increase, and the homogenizing may be performed many times (e.g., 2 to 4 times) at the same pressure. As another example, components of the first reagent other than the first solvent are also mixed and sheared before mixing with the first solvent.

In a sixth aspect, the present invention provides a use of the fat emulsion in preparation of a peritoneal dialysate. As described above, the small-particle-sized oil phase of the system is utilized as adsorption material in the peritoneal dialysate to effectively enhance the binding capacity of the peritoneal dialysate system to the protein-bound toxins, so that the protein-bound toxin removal capacity of the peritoneal dialysate is improved, and the peritoneal dialysate can be used for peritoneal dialysis.

In the use provided by the present invention, the fat emulsion is the fat emulsion combination reagent provided by the fourth aspect of the present invention.

In one embodiment, the use comprises mixing the first reagent with the second reagent of the fat emulsion combination reagent to provide a peritoneal dialysate. In an embodiment, after the mixing of the first reagent and the second reagent, a pH of the mixed solution ranges from 5.0 to 8.0, 5.0 to 5.5, 5.5 to 6.0, 6.0 to 6.5, 6.5 to 7.0, 7.0 to 7.5, or 7.5 to 8.0. In an embodiment, an osmotic pressure of the mixed solution ranges from 300 to 500 mOsmol/L, 300 to 400 mOsmol/L, or 400 to 500 mOsmol/L.

In a further preferred embodiment, the use comprises putting the first reagent of the fat emulsion combination reagent provided by the fourth aspect of the present invention in a first chamber bag, and putting the second reagent in at least one second chamber bag. When the base donor of the second reagent is sodium lactate, the second reagent is put in a second chamber bag; when the base donor of the second reagent is sodium bicarbonate or a mixture of sodium lactate and sodium bicarbonate, the penetrating agent and the first portion of the electrolyte of the second reagent are put in a second chamber bag, and the base donor and the second portion of the electrolyte of the second reagent are put in another second chamber bag.

The fat emulsion dialysate provided by the present invention has a better advantage in protein-bound toxin removal as compared with conventional dialysis. Moreover, this fat emulsion dialysate is not only easy to prepare, has low cost, but also has good stability and safety. It maintains stable at room temperature for 14 days without obvious precipitation, and it can become a hemodialysis dialysate or a peritoneal dialysate with wide application prospects and good industrialization prospects.

Hereinafter the invention of the present application is further described by reference to the examples, and it is not intended to limit the scope of the present application.

The information on the main reagents used in the examples is as follows:

Bovine serum albumin BSA (sigma, purity≥98%);

P-cresol (sigma, CAS NO: 106-44-5);

p-Cresyl sulfate (pCS, sigma, CAS NO: 3233-58-7);

indoxyl sulfate (IS, sigma, CAS NO: 608-08-2);

Potassium indoxyl sulfate (IS, sigma, CAS NO: 2642-37-7);

Indolyl-3-acetic acid (3-IAA, sigma, CAS NO: 87-51-4);

Soybean oil (Aladdin, CAS NO: 8001-22-7);

Medium-chain triglyceride (MCT, C8: 58.4%, C10: 41.5%, C12: 0.1%);

Glycerin (CAS NO: 56-81-5);

Egg yolk lecithin (with a content of phosphatidylcholine of about 80%, CAS NO: 93685-90-6);

Sodium oleate (cis-9-octadecen-1-ol, CAS NO: 143-19-1);

α-tocopherol (Aladdin, CAS NO: 59-02-9).

Pentobarbital sodium (Sigma, CAS NO: 4390-16-3);

Mouse embryonic fibroblasts (NIH-3T3);

C57BL/6 mice (Shanghai JieSiJie Laboratory Animal Co., Ltd.).

The control dialysate used in the Examples 8-13 was glucose peritoneal dialysate, specifically is 1.5% glucose-low calcium peritoneal dialysis solution (Baxter International Inc.).

In the examples 1-7, high-performance liquid chromatography (HPLC) was used to establish the IS and PCS methodologies, and an Agilent Type 1100 HPLC was used to detect the concentrations of various toxins. During the detection, the samples comprising albumin and fat emulsion were processed by means of: sucking 200 μL of the sample solution, adding 600 μL of acetonitrile to precipitate the protein or fat emulsion, centrifuging at 4° C. at 12,000 rpm for 20 min, and sampling the supernatant for detection.

In the examples 8-13, the concentration of protein-bound toxins such as IS and pCS were measured by using a Waters e2695 high-performance liquid chromatograph and a Shimadzu RF-20A fluorescence detector. During the detection, the samples were processed by means of: sucking 50 μL of the sample solution, adding 5 μL of 35% perchloric acid to precipitate the protein or fat emulsion, centrifuging at 12,000 rpm for 10 min, collecting 20 μL of supernatant, diluting the supernatant to 100 μL for detection. The excitation wavelength of p-Cresyl sulfate (pCS) is 265 nm and the emission wavelength is 290 nm, the excitation wavelength of indoxyl sulfate (IS) is 278 nm and the emission wavelength is 348 nm.

The statistical method used in the examples was as follows: the detection results were processed with SPSS 21.0 statistical software, and the data was expressed by mean±standard deviation. Independent-sample t test was used for comparison between the two groups, and a single-factor analysis of variance was used for comparison among multiple groups. $p < 0.05$ was considered statistically significant.

Example 1

An aqueous phase and an oil phase were prepared, respectively. 5.5 g of soybean oil, 4.5 g of medium-chain triglyceride, and 0.15 g of α-tocopherol were weighed, mixed, and stirred so that they were fully dissolved to serve as the oil phase. 0.13 g of sodium oleate, 0.9 g of glycerin, and a certain mass percent (0.4, 0.8, 1, 2, and 3%) of egg yolk lecithin were weighed, added into a certain volume of solution (water or dialysate), and stirred so that they were uniformly dissolved to serve as the aqueous phase. The oil phase was pretreated by high-speed shearing. The temperature of the aqueous phase was raised to 70° C., and then the oil phase was slowly injected into the aqueous phase. The mixture was subjected to high-speed shearing for 10 min. The obtained solution after shearing was subjected to gradient homogenization (600, 800, and 1000, twice at each gradient) under a pressure of 600 to 1000 bar by using a high-pressure homogenizer to provide a fat emulsion dialysate. The fat emulsion dialysate was used in cooperation with a 5% sodium bicarbonate solution during in vitro simulated dialysis. The specific ratio was 6.25 mL of 5% sodium bicarbonate solution per 100 mL of the fat emulsion dialysate.

Example 2

Figure 2:
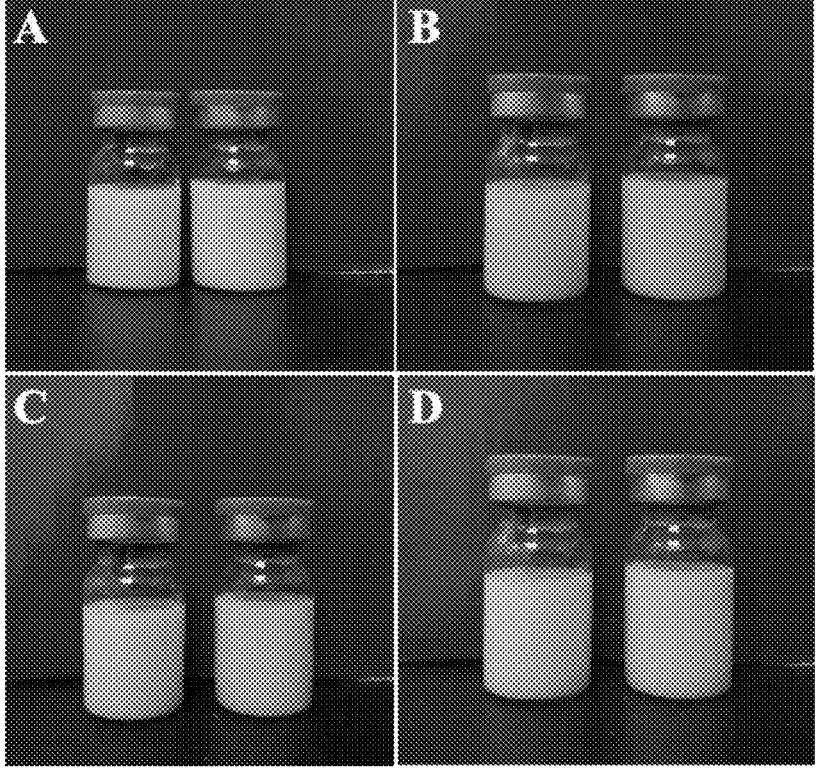
FIG. 2 shows a schematic diagram showing a stability of the fat emulsion in Example 2 of the present invention.

The hydration kinetic size of the fat emulsion in the fat emulsion dialysates with different phospholipid contents prepared according to the method described in Example 1 was detected by Malvern particle size analyzer, and the results were shown in Table 1. The surface morphology of the fat emulsion particles with 3% phospholipid content was observed by a transmission electron microscope, and the results were shown in FIG. 1. The apparent morphology (stability) of the fat emulsion during standing at room temperature for 21 days was shown in FIG. 2 (where A: Day 1; B: Day 4; C: Day 7; D: Day 14).

TABLE 1

| The Particle Size of Fat Emulsions with Different Phospholipid Contents | |
| --- | --- |
| Phospholipid Content, % | Particle Size of Fat Emulsion, nm |
| 0.4 | 199.9 |
| 0.8 | 181.2 |
| 2.0 | 170.5 |

Example 3

The binding rate to PBUTs was detected as follows:

The fat emulsion dialysates with different phospholipid contents (1%, 2%, and 3%) prepared in Example 1 were selected, and the working concentrations of the protein-bound toxins were set as p-cresol (200 μmol/L), IS (150 μmol/L), and IAA (20 μmol/L), respectively. According to the above concentrations, the toxins were added into the fat emulsion dialysates with different phospholipid concentrations, and co-cultured for 1 hour. 400 μL of the co-culture solution were added into an ultrafiltration tube (Millipore Company, Mw=3 K), and subjected to centrifugation at 25° C. at 12000 rpm for 30 minutes. The toxin concentrations in the samples before and after ultrafiltration and the toxin concentrations of the filtrate were respectively detected by HPLC (n=5), and the direct adsorption rates of the materials to the toxins were calculated. The calculation formula was as follows:

Direct Adsorption Rate %=(Total Concentration Before Ultrafiltration−Concentration of Filtrate After Ultrafiltration)/Total Concentration Before Ultrafiltration×100%

Figure 3:
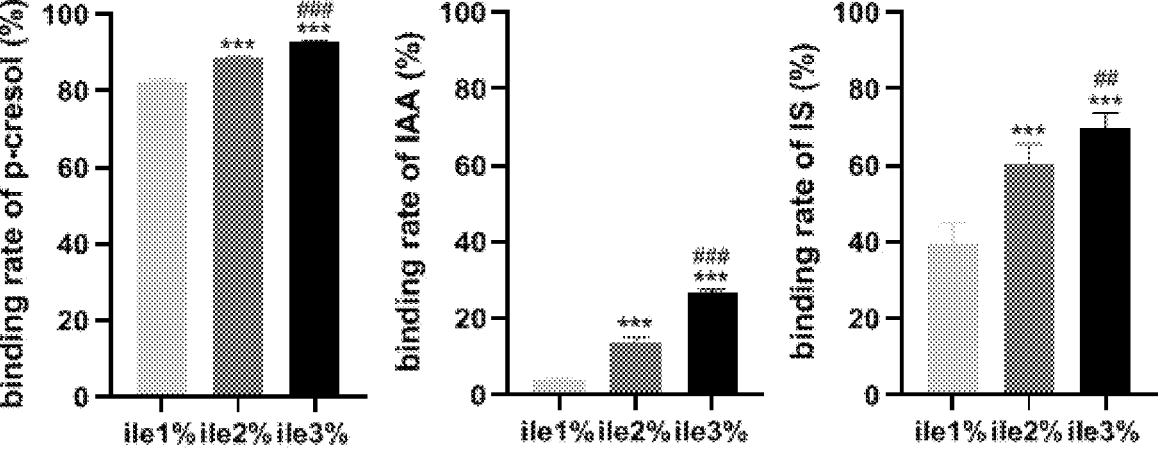
FIG. 3 shows a schematic diagram of a capacity of fat emulsions with different phospholipid contents binding to three protein-bound toxins (p-cresol, IAA, and IS) in Example 3 of the present invention.

The detection results of the binding rate to PBUTs were specially shown in FIG. 3, where ile1%, ile2%, and ile3% were the 50 g/L fat emulsions with phospholipid content of 1%, 2%, and 3%, respectively. *P<0.001 as compared with the ile1%; and ##p<0.01, ###p<0.001 as compared with the ile2%. As seen in FIG. 3**, 50 g/L fat emulsions with phospholipid contents of 1%, 2%, and 3% have binding rates to the IS of about 39.4%, 60.42%, and 69.9%, respectively, have binding rates to the IAA of about 3.83%, 13.82%, and 27.06%, respectively, and have binding rates to the p-cresol of about 82.4%, 88.76%, and 92.61%, respectively. It can be seen that with the increase of phospholipid content, the direct adsorption rate of the fat emulsion to the protein-bound toxin increases.

Example 4

The removal effect to protein-bound toxins was evaluated by Equilibrium Plate Dialysis:

According to the results of direct adsorption rate, the fat emulsion dialysate with a phospholipid concentration of 3% (the same as Example 3) was selected for the next test. The indirect removal capacity of the material to various protein-bound toxins was evaluated by Rapid Equilibrium Dialysis (RED) (Thermo company, Mw=8 K). 40 g/L of HSA solution was prepared, and added to the protein-bound toxins p-cresol (200 μmol/L), IS (150 μmol/L), and IAA (20 μmol/L), respectively, followed by incubation at room temperature for 1 hour. Subsequently, 300 μl of HSA solution containing various protein-bound toxins as described above was added into the sample chamber of the RED plate, and 500 μl of fat emulsion with 3% phospholipid concentration or common sodium bicarbonate replacement solution (negative control) was added to the dialysate chamber. The RED was placed on a shaker, dialyzed at equilibrium at 37° C. and 250 rpm for 4 hours. The samples were taken for detection (n=5). Samples were taken from the sample chamber and dialysate chamber, respectively, and the toxin concentration was detected by HPLC. The indirect removal rate to toxin was calculated by the following formula:

Toxin removal rate (%)=(Toxin concentration at the sample side before the dialysis−Toxin concentration at the sample side after dialysis)/Toxin concentration at the sample side before the dialysis×100%

Figure 4:
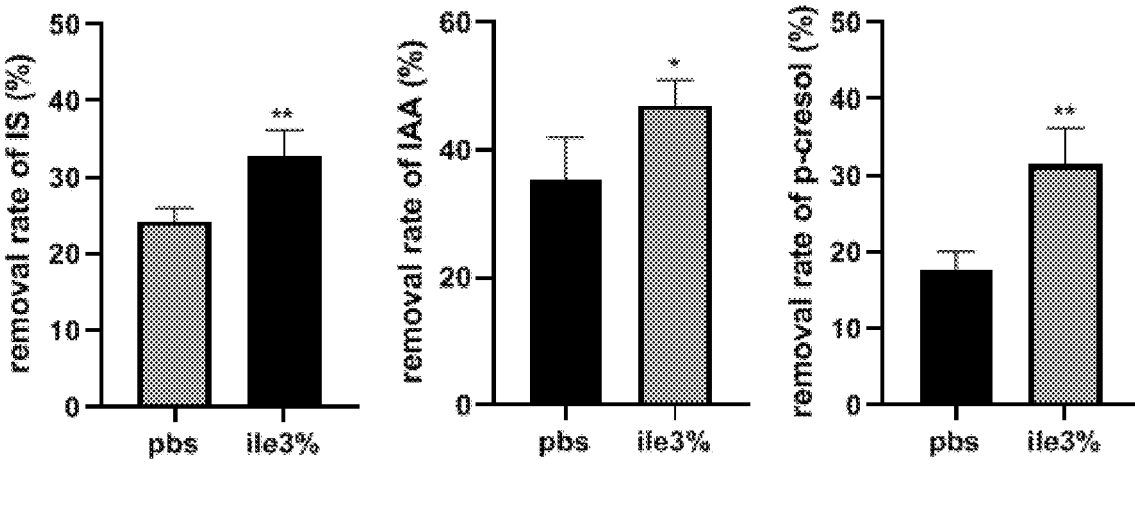
FIG. 4 shows a schematic diagram of a capacity of fat emulsion with 3% phospholipid content for removing three protein-bound toxins (p-cresol, IAA, and IS) in Example 4 of the present invention.

The results of removal effect to protein-bound toxins evaluated by equilibrium plate dialysis were shown in FIG. 4. As seen in FIG. 4, the indirect removal rates of common sodium bicarbonate replacement solution to IS, IAA, and p-cresol were about 24.28%, 35.15%, and 17.62% respectively, while the indirect removal rates of fat emulsion with 3% phospholipid concentration to IS, IAA, and p-cresol were about 32.8% (p<0.01), 47.02% (p<0.05), and 31.52% (p<0.01), respectively. It can be seen that 50 g/L of fat emulsion can significantly improve the removal rate to protein-bound toxins as compared with common sodium bicarbonate replacement solution.

Example 5

Figure 5:
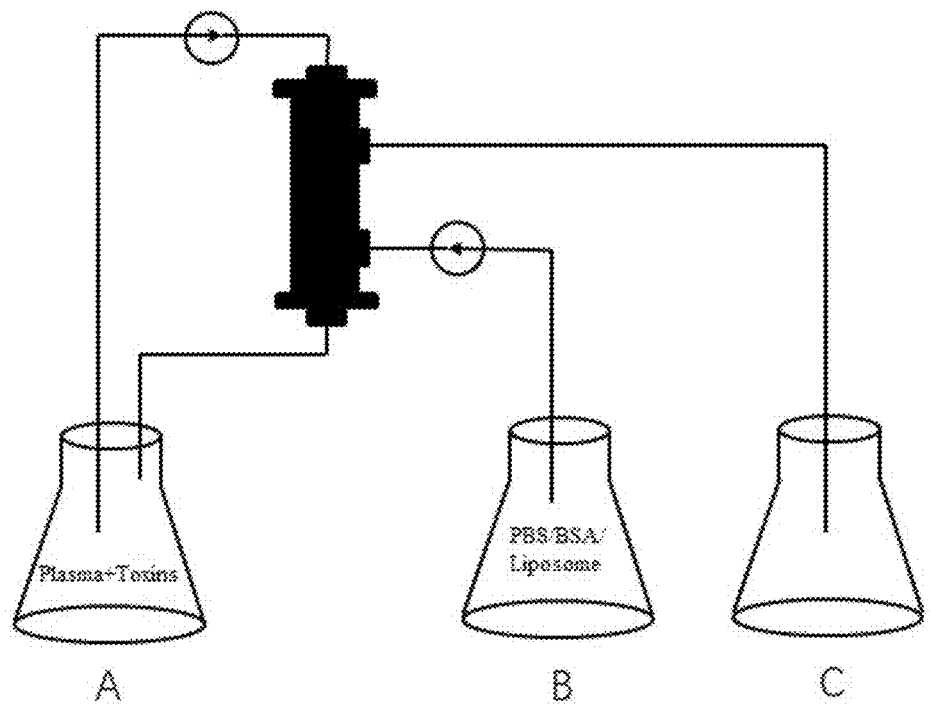
FIG. 5 shows a schematic diagram of an in vitro simulated dialysis device in Example 5 of the present invention.

The removal effects to protein-bound toxins were evaluated by simulated hemodialysis in vitro:

An in vitro dialysis model containing a small dialyzer with polysulfone membrane (Mw=20 KDa) (as shown in FIG. 5) was constructed to simulate the hemodialysis in vitro. 40 g/L of BSA solution was prepared, and added to the protein-bound toxins p-cresol (200 μmol/L), IS (150 μmol/L), and IAA (20 μmol/L), respectively, followed by incubation at room temperature for 1 hour. Then 40 mL of BSA solution containing the protein-bound toxins was added to the blood side, and the fat emulsion dialysate with phospholipid concentration of 3% or common sodium bicarbonate dialysate was added to the dialysate side. The flow rate was set to 5 ml/min at the blood side, and 2.5 ml/min at the dialysate side. Samples were taken from the blood side and the dialysate side at 0, 10, 30, 60, 120, 180, and 240 minutes after extracorporeal circulation, and the concentrations of various toxins in the samples were measured. The change rules of various toxin concentrations at the blood and dialysate sides during extracorporeal hemodialysis within 4 hours were evaluated. The dialysis removal rates of common sodium bicarbonate dialysate and the fat emulsion dialysate to the various toxins were calculated and compared. The results were particularly shown in FIG. 6.

Figure 6:
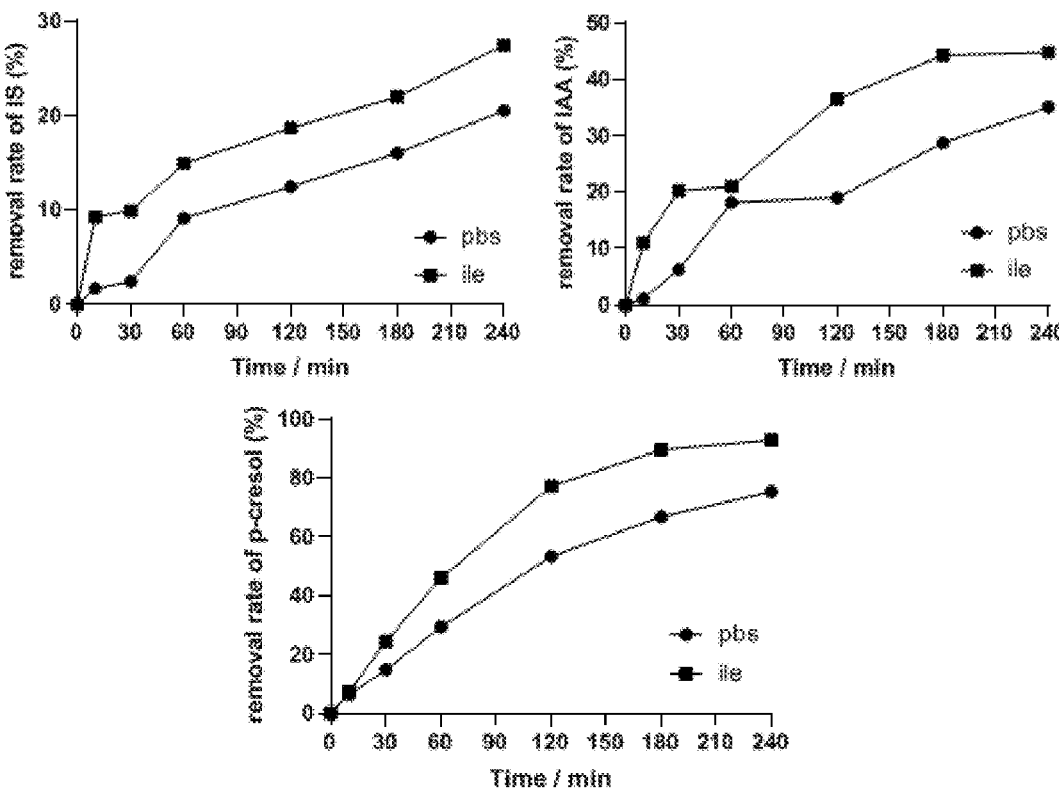
FIG. 6 shows a schematic diagram of a capacity of fat emulsion with 3% phospholipid content for removing three protein-bound toxins (p-cresol, IAA, and IS) in Example 5 of the present invention under a condition of in vitro simulated dialysis.

It can be seen from FIG. 6 that the removal rates to IS, IAA, and p-cresol of the common dialysate group were about 20.53%, 35.13%, and 75.34%, respectively, while the removal rates to IS, IAA, and p-cresol of the fat emulsion dialysate group were about 27.45%, 44.83%, and 92.99%, respectively by in vitro simulated hemodialysis for 4 hours.

It can be seen that the removal effect of the fat emulsion dialysate group is higher than that of the common dialysate group.

Example 6

Hemolytic Test:

The biocompatibility of the fat emulsion was verified by studying the passive hemolysis behavior of the fat emulsion. Red blood cells collected from fresh human blood were diluted to 5% (v/v) by using a PBS solution. 300 μL of red blood cell suspension and 500 μL of the fat emulsion with 3% phospholipid concentration, PBS (negative control) or ddH2O (positive control) solution were added to the blood side and the sample side of the RED plate, respectively, and then shaken at 37° C. for 4 hours. After the completion of the experiment, the red blood cells were collected, and centrifuged at 3700 rpm for 5 min. 100 μL of supernatant was added to a 96-well plate. At the detection wavelength of 541 nm, the absorbance (OD value) of the fat emulsion group, the positive control group, and the negative control group was detected, which were designated as $A_{test}$, $A_{control}$, and $A_{blank}$, respectively. The passive hemolysis of the fat emulsion was calculated according to the following formula.

$$Hemolysis\ (\%)=(A_{test}-A_{blank})/(A_{control}-A_{blank})\times100\%$$

According to the experimental results, the passive hemolysis of the fat emulsion was 0.60±1.33%.

Example 7

Cytotoxicity Test:

The biocompatibility of the fat emulsion with a phospholipid concentration of 3% was studied by CCK-8 cytotoxicity test using mouse embryonic fibroblasts (NIH-3T3). Cells were inoculated into a 96-well plate with a density of 10000, and grew adherently for 24 h. The culture medium was replaced by an ordinary DMEM medium or a DMEM medium solution containing the fat emulsion with a phospholipid concentration of 3% (0.1%, v/v). After 24 hours of co-culture, 10 μL of CCK-8 solution was added to the corresponding wells, and the cells were cultured at 37° C. for an additional 1 hour. The absorbance values (OD values, recorded as $A_{Test}$) were detected at 450 nm. The OD values of blank wells and cell wells with the pure medium were detected (recorded as $A_{Blank}$ and $A_{CTR}$, respectively). Cytotoxicity was calculated according to the following formula:

$$Cytotoxicity\ (\%)=(A_{Test}-A_{Blank})/(A_{CTR}-A_{Blank})\times100\%$$

Figure 7:
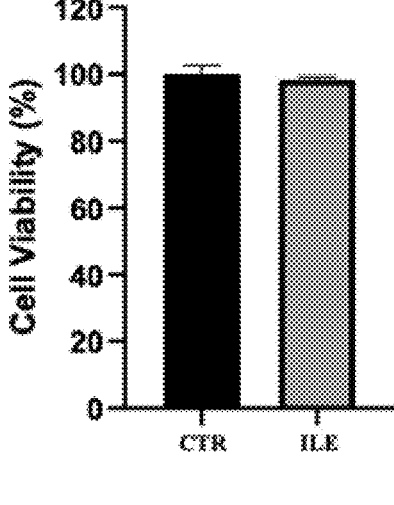
FIG. 7 shows a schematic diagram of a cytotoxicity of fat emulsion in Example 7 of the present invention.
Figure 8:
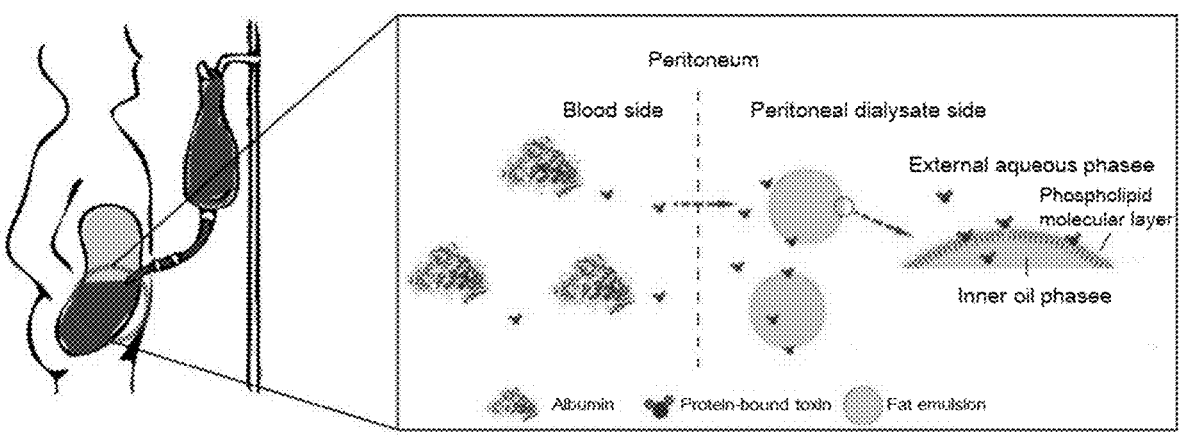
FIG. 8 shows a schematic diagram of a principle of the fat emulsion combination reagent serving as a peritoneal dialysate for protein-bound toxin removal of the present invention.

The experimental results were shown in FIG. 7. According to the experimental results, after co-incubation with the fat emulsion, the cell viability was 98.4±0.86%, showing good biocompatibility.

Example 8

Figure 9:
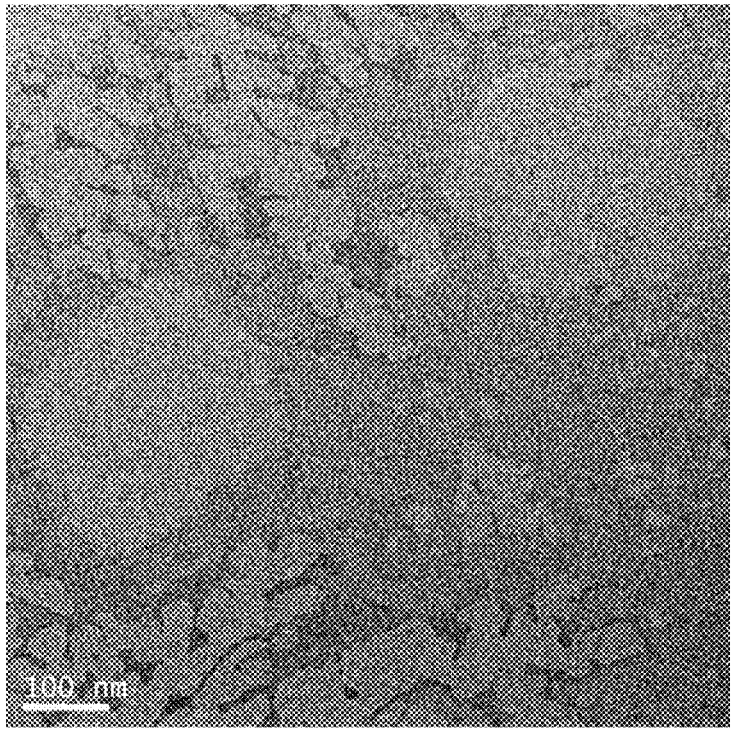
FIG. 9 shows a schematic diagram of fat emulsion particles observed by a transmission electron microscope in Example 8 of the present invention.

5.5 g of soybean oil, 4.1 g of medium-chain triglycerides, 0.13 g of α-tocopherol, 0.15 g of sodium oleate, and 1 g of egg yolk lecithin were mixed and stirred, so that they were uniformly dissolved. The mixture was pre-treated with high-speed shearing at 10000 to 20000 r/min for 5 min. 90 mL of water acted as the first solvent, the mixture and the first solvent were heated to 75° C., then the mixture was slowly added into the first solvent, and the system was subjected to high-speed shearing at 10000 to 20000 r/min for 15 min. The sheared system was gradually homogenized (800, 1000, 1200, twice at each gradient) by using a high-pressure homogenizer under 800-1200 bar to obtain the first reagent sample 1#, which was placed in the first chamber bag. 560 mg of NaCl, 19 mg of CaCl₂, 5.5 mg of MgCl₂, 1575 mg of glucose, and 523.3 mg of sodium lactate were dissolved in 20 ml of water to serve as the second reagent sample 1#. As the base donor of the second reagent sample 1# was sodium lactate, the second reagent was placed in the second chamber bag. The first reagent sample 1# was mixed with the second reagent sample 1# on the spot to obtain peritoneal dialysate sample 1#. Fat emulsion particles of peritoneal dialysate sample 1#, which was observed by a transmission electron microscope, were shown in FIG. 9. From FIG. 9, it can be seen that the fat emulsion particles are spherical nanoparticles with a particle size of about 200 nm.

Example 9

5.4 g of soybean oil, 4.0 g of medium chain triglycerides, 0.12 g of α-tocopherol, 0.16 g of sodium oleate, and 3 g of egg yolk lecithin were mixed and stirred to dissolve fully, and the mixture was pre-treated by high-speed shearing at 10000-20000 r/min for 8 min. 85 mL of water acted as the first solvent, the mixture and the first solvent were heated to 65° C., then the mixture was slowly added into the first solvent, and the system was subjected to high-speed shearing at 10000 to 20000 r/min for 20 min. The sheared system was gradiently homogenized (800, 1000, 1200, twice at each gradient) by using a high-pressure homogenizer under 800-1200 bar to obtain the first reagent sample 2#, which was placed in the first chamber bag. 558 mg of NaCl, 18.5 mg of CaCl₂, 5.2 mg of MgCl₂, and 1555 mg of glucose were dissolved in 10 ml of water to serve as the second reagent sample 2#-1. 280 mg of sodium lactate and 159 mg of sodium bicarbonate were dissolved in 10 ml of water to serve as the second reagent sample 2#-2. As the base donor of the second reagent was a mixture of sodium lactate and sodium bicarbonate, the second reagent sample 2#-1 was placed in a second chamber bag and the second reagent sample 2#-2 was placed in another second chamber bag. The first reagent sample 2#, the second reagent sample 2#-1, and the second reagent sample 2#-2 were mixed on the spot to obtain peritoneal dialysate sample 2#.

Example 10

Representative protein-bound toxins of uremia, i.e. p-Cresyl sulfate (pCS) and indoxyl sulfate (IS), were added to 400 μL of glucose peritoneal dialysate and the peritoneal dialysate sample 1# obtained in Example 8, respectively, and then were incubated for 30 min, where the concentration of p-Cresyl sulfate was 200 μmol/L, the concentration of indoxyl sulfate was 150 μmol/L, and the glucose peritoneal dialysate was the control sample. The incubated samples were transferred to 0.5 mL ultrafiltration tubes (10 kD, Millipore), centrifuged at 4° C. at 12000 rpm for 30 min, and the ultrafiltrate was extracted. The toxin concentrations in the samples before and after ultrafiltration and the toxin concentrations of the filtrate were respectively detected by HPLC (n=6), and the binding rates of the materials to the toxins were calculated. The calculation formula was as follows:

Binding Rate %=(Total Concentration Before Ultrafiltration−Concentration of Filtrate After Ultrafiltration)/Total Concentration Before Ultrafiltration×100%

Figure 10:
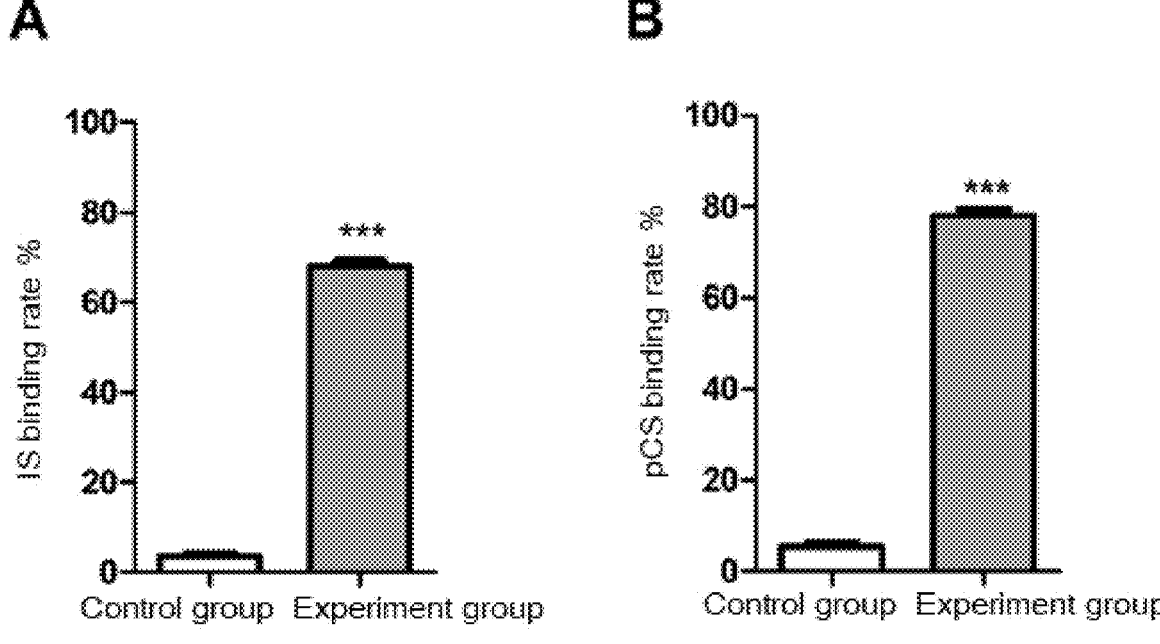
FIG. 10 shows a schematic diagram of an adsorption rate of the fat emulsion combination reagent, which serves as a peritoneal dialysate, for two protein-bound toxins using ultrafiltration tube method in Example 10 of the present invention, where A is IS and B is pCS.

The detection results of the binding rate to PBUTs were shown in FIG. 10. The fat emulsion serving as peritoneal dialysate had a binding rate to the IS of about 68.09±2.00%, which was significantly higher than that of the blank control group (i.e. 3.53±1.58%) (*p<0.001). The fat emulsion serving as peritoneal dialysate had a binding rate to the pCS of about 78.04±2.42%, which was also significantly higher than that of the blank control group (i.e. 5.47±1.86%) (*p<0.001), indicating that the fat emulsion has a good binding capacity to protein-bound toxins.

Example 11

Representative protein-bound toxins of uremia, i.e. pCS (200 μmol/L) and IS (150 μmol/L), were added to 40 g/L of BSA solution, and followed by incubation for 30 min. Subsequently, 300 μl of BSA solution containing protein-bound toxins as described above was added into the sample chamber of the RED plate, and 500 μl of glucose peritoneal dialysate (control sample) or the peritoneal dialysate sample 1# obtained in Example 8 was added to the dialysate chamber. The RED was placed on a shaker, dialyzed at equilibrium at 37° C. and 250 rpm for 4 hours. The toxin concentrations within the dialysate chamber before and after equilibrium dialysis were detected using high-performance liquid chromatography, and the removal rate of each peritoneal dialysate to the protein-bound toxins was calculated by the following formula:

Toxin removal rate (%)=(Toxin concentration at the sample side before the dialysis−Toxin concentration at the sample side after dialysis)/Toxin concentration at the sample side before the dialysis×100%

Figure 11:
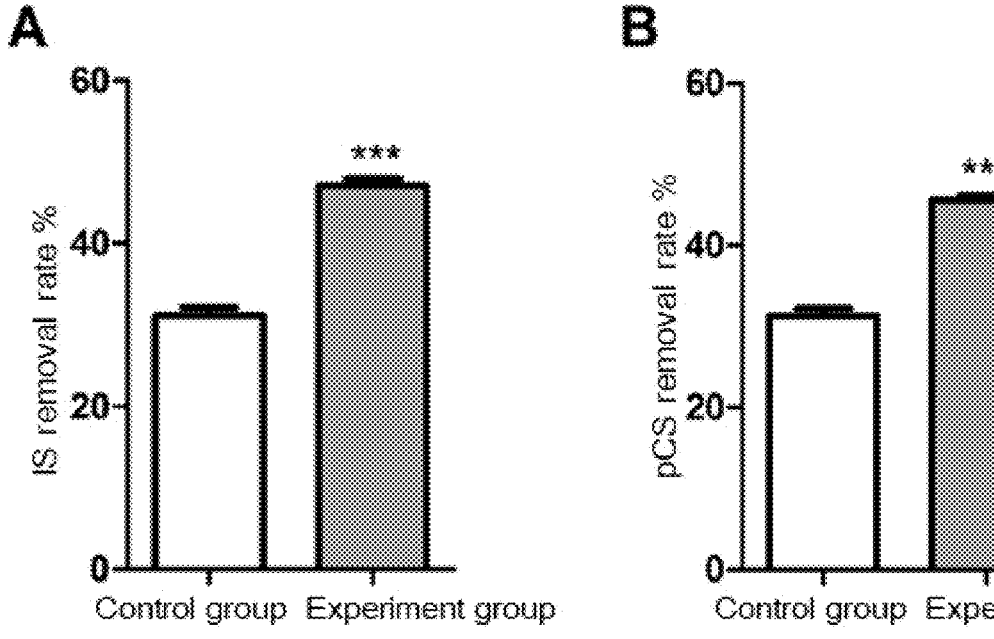
FIG. 11 shows a schematic diagram of a clearance rate of the fat emulsion combination reagent, which serves as a peritoneal dialysate, for the two protein-bound toxins using rapid equilibrium plate dialysis method in Example 11 of the present invention, where A is IS and B is pCS.

The results of the removal effect on protein-bound toxins were shown in FIG. 11. The fat emulsion serving as peritoneal dialysate had a removal rate to the IS of about 47.09±1.57%, which was significantly higher than that of the blank control group (i.e. 31.11±1.83%) (*p<0.001). The fat emulsion serving as peritoneal dialysate had a removal rate to the pCS of about 45.54±0.89%, which was also significantly higher than that of the blank control group (i.e. 31.27±1.62%) (*p<0.001), indicating that the fat emulsion as a peritoneal dialysate dramatically improves the in vitro clearance of protein-bound toxins.

Example 12

Twelve 16-week c57 mice, weighing 25-30 g, were fed in SPF class animal rooms under ambient temperature, where the temperature was 20-25° C. and air humidity was 30-60%. Mice were arranged in individually ventilated cage boxes (IVC) without restriction of their food and water intake.

The mice were randomly divided into 2 groups with 6 mice in each group. The two groups were (1) the control group and (2) the experimental group, where standard peritoneal dialysate (i.e. glucose peritoneal dialysate) was administered in the control group, and peritoneal dialysate sample 1# obtained in Example 8 was administered in the experimental group.

Mice were anesthetized with 1% pentobarbital sodium (0.5 ml/100 g, intramuscular injection) and fixed on a pet pad in the supine position. The pet pad was turned on to a mid-range to maintain the body temperature of the mice during the operation. After skin preparation, the skin of the mice was disinfected with Anerdian, an approximately 2-mm incision was slit in the skin along the midline of the abdomen, subcutaneous tissue and muscle layer were bluntly separated, and each mouse was slowly injected with 60 mL/kg of peritoneal dialysate preheated to 37° C. The abdominal incision was closed with hemostatic forceps, and peritoneal dialysis was performed for 4 hours.

After 4 hours of peritoneal dialysis, 300 μL of blood was extracted from the right ventricle of the mice. The serum was separated by centrifugation at 4000 rpm for 10 min after resting on ice for 30 min. The peritoneal dialysate was collected from the peritoneal cavity of the mice. The protein-bound toxin concentrations in the serum and peritoneal dialysate of each group of mice were measured separately using high-performance liquid chromatography, and the clearance rate of each peritoneal dialysate to the protein-bound toxins was calculated by the following formula:

$$\text{Toxin clearance rate (\%)}=\text{Peritoneal dialysate toxin concentration/Serum toxin concentration}\times100\%$$

Figure 12:
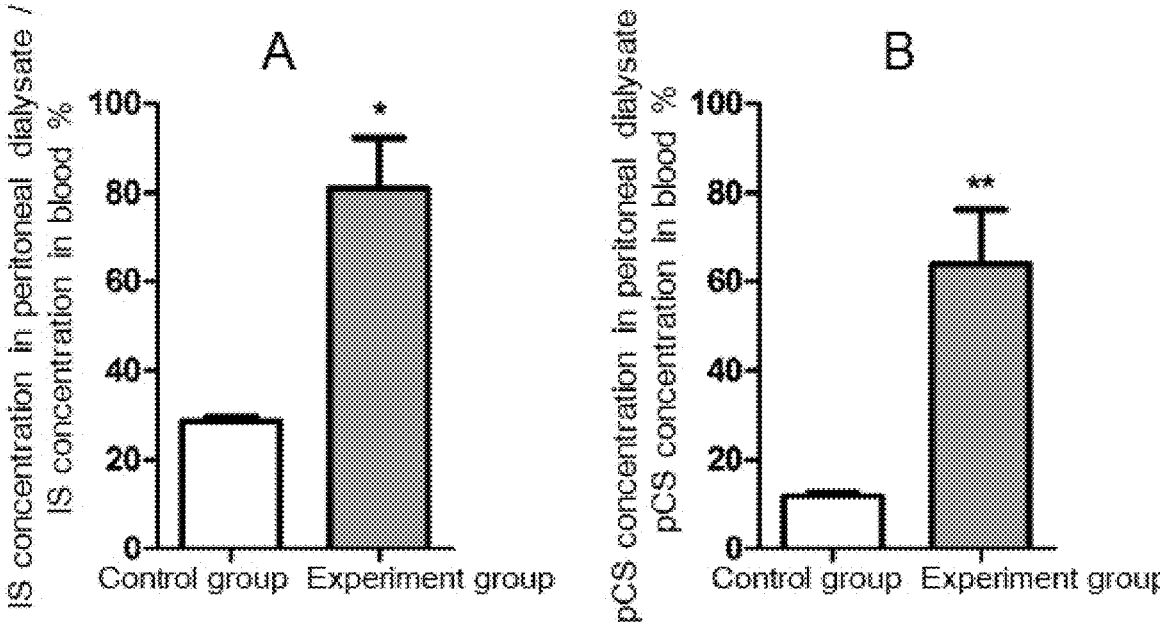
FIG. 12 shows a schematic diagram of the clearance rate of the fat emulsion combination reagent, which serves as a peritoneal dialysate, for protein-bound toxins in mice in Example 12 of the present invention, where A is IS and B is pCS.

The results of the toxin clearance rate were shown in FIG. 12. The fat emulsion serving as peritoneal dialysate had a clearance rate to the IS of about 80.99±25.27%, which was significantly higher than that of the blank control group (i.e. 28.53±2.05%) (*p<0.05). The fat emulsion serving as peritoneal dialysate had a clearance rate to the pCS of about 63.86±24.67%, which was also significantly higher than that of the blank control group (i.e. 11.87±1.53%) (**p<0.01), indicating that the fat emulsion as a peritoneal dialysate dramatically improves the clearance of protein-bound toxins in mice.

Example 13

The biocompatibility of the peritoneal dialysate, for example, the peritoneal dialysate prepared in Example 9, with a phospholipid concentration of 3% was studied by CCK-8 cytotoxicity test using mouse embryonic fibroblasts (NIH-3T3). Cells were inoculated into a 96-well plate with a density of 10000, and grew adherently for 24 h. The culture medium was replaced by an ordinary DMEM medium or a DMEM medium solution containing the fat emulsion with a phospholipid concentration of 3% (0.1%, v/v). After 24 hours of co-culture, 10 μL of CCK-8 solution was added to the corresponding wells, and the cells were cultured at 37° C. for an additional 1 hour. The absorbance values (OD values, recorded as $A_{Test}$) were detected at 450 nm. The OD values of blank wells and cell wells with the pure medium were detected (recorded as $A_{Blank}$ and $A_{CTR}$, respectively). Cytotoxicity was calculated according to the following formula:

$$\text{Cytotoxicity (\%)}=(A_{Test}-A_{Blank})/(A_{CTR}-A_{Blank})\times100\%$$

Figure 13:
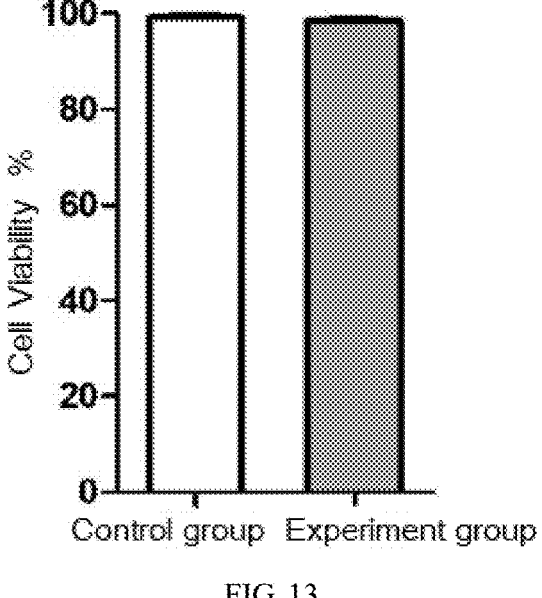
FIG. 13 shows a schematic diagram of a cytotoxicity of the fat emulsion combination reagent using CCK8 cytotoxicity assay in Example 13 of the present invention.

The results of cytotoxicity experiments were shown in FIG. 13. According to the experimental results, after co-incubation with the fat emulsion, the cell viability was 98.4±0.43%, showing good biocompatibility.

To sum up, the present invention effectively overcomes various shortcomings in the prior art and has high industrial utilization value.

The above examples are only for exemplarily illustrating the principles and efficacy of the present invention, but not for restricting the present invention. Any person skilled in the art can make modifications or variations to the above examples without departing the spirit and scope of the present invention. Thus, all the equivalent modifications or variations made by persons of ordinary skills in the related technical field without departing the spirit and technical concept disclosed by the present invention are still within the appended claims of the present invention.

What is claimed is:

1. A method for preparing a hemodialysis dialysate, comprising preparing a fat emulsion dialysate, wherein the fat emulsion dialysate comprises a long-chain fat emulsion oil, a medium-chain triglyceride, an anti-oxidant, sodium oleate, glycerin, phospholipid, and a solvent; and formulating a hemodialysis dialysate by incorporating the fat emulsion dialysate.

2. The method of claim 1, wherein the fat emulsion dialysate comprises, by weight percent,
   3 to 15% of the long-chain fat emulsion oil;
   1.5 to 9% of the medium-chain triglyceride;
   0.05 to 0.3% of the anti-oxidant;
   0.05 to 0.3% of sodium oleate;
   0.2 to 2% of glycerin;
   1 to 12% of phospholipid; and
   65 to 95% of the solvent.

3. The method of claim 1, wherein the long-chain fat emulsion oil is selected from one or a combination of olive oil and soybean oil; and/or
   a total content of acid and decanoic acid in the medium-chain triglyceride is no less than 99 wt %; and/or
   the anti-oxidant is one or a combination of α-tocopherol and squalene.

4. The method of claim 1, wherein the phospholipid is selected from lecithins.

5. The method of claim 1, wherein the solvent is an aqueous solvent, the aqueous solvent comprises water, and further comprises one or more of sodium chloride, potassium chloride, calcium chloride, magnesium chloride, and glucose.

6. The method of claim 1, wherein the fat emulsion dialysate is an oil-in-water system.

7. The method of claim 6, wherein a fat emulsion particle size in the fat emulsion dialysate is 150 to 500 nm.

8. A fat emulsion dialysate, comprising a long-chain fat emulsion oil, a medium-chain triglyceride, an anti-oxidant, sodium oleate, glycerin, phospholipid, and a solvent, wherein the fat emulsion dialysate comprising, by weight percent,
   3 to 15% of the long-chain fat emulsion oil;
   1.5 to 9% of the medium-chain triglyceride;
   0.05 to 0.3% of the anti-oxidant;
   0.05 to 0.3% of sodium oleate;
   0.2 to 2% of glycerin;
   1 to 12% of phospholipid; and
   65 to 95% of the solvent.

9. The fat emulsion dialysate of claim 8, wherein the long-chain fat emulsion oil is selected from one or a combination of olive oil and soybean oil; and/or
   a total content of acid and decanoic acid in the medium-chain triglyceride is no less than 99 wt %; and/or
   the anti-oxidant is one or a combination of α-tocopherol and squalene.

10. The fat emulsion dialysate of claim 8, wherein the phospholipid is selected from lecithins.

11. The fat emulsion dialysate of claim 8, wherein the solvent is an aqueous solvent, the aqueous solvent comprising water, and further comprising one or more of sodium chloride, potassium chloride, calcium chloride, magnesium chloride, and glucose.

12. The fat emulsion dialysate of claim 8, wherein the fat emulsion dialysate is an oil-in-water system.

13. The fat emulsion dialysate of claim 12, wherein a fat emulsion particle size in the fat emulsion dialysate is 150 to 500 nm.

14. A method for preparing the fat emulsion dialysate of claim 8, comprising: providing an oil phase and an aqueous phase, mixing the oil phase with the aqueous phase, and homogenizing to provide the fat emulsion dialysate.

15. The method of claim 14, wherein the mixing and/or homogenizing is carried out at a temperature of 50 to 90° C.; and/or the oil phase and the aqueous phase are thoroughly mixed by high-speed shearing at a high-speed shear rate of 10000 to 20000 rpm and a shear time of 5 to 30 min; and/or the homogenizing is carried at a pressure of 200 to 1000 bar.

16. The method of claim 1, wherein a total content of acid and decanoic acid in the medium-chain triglyceride is no less than 99.5 wt %; and/or wherein the phospholipid is one or a combination of soybean lecithin and egg yolk lecithin.

17. The method of claim 1, wherein a total content of acid and decanoic acid in the medium-chain triglyceride is no less than 99.9 wt %.

18. The fat emulsion dialysate of claim 8, wherein a total content of acid and decanoic acid in the medium-chain triglyceride is no less than 99.5 wt %; and/or wherein the phospholipid is one or a combination of soybean lecithin and egg yolk lecithin.

19. The fat emulsion dialysate of claim 8, wherein a total content of acid and decanoic acid in the medium-chain triglyceride is no less than 99.9 wt %.

20. The method of claim 1, wherein the fat emulsion dialysate is an emulsion system which utilizes a nano-particle-sized oil phase as adsorptive material in dialysate to enhance the binding capacity of the dialysate system to the protein-bound toxins, thereby improving the protein-bound toxin removal capacity of the dialysate.

* * * * *